(12) United States Patent
Jahangir et al.

(10) Patent No.: US 7,414,059 B2
(45) Date of Patent: Aug. 19, 2008

(54) PYRAZOLYL AND IMIDAZOLYL PYRIMIDINES AS CRF ANTAGONISTS

(75) Inventors: Alam Jahangir, San Jose, CA (US); Counde O'Yang, Sunnyvale, CA (US)

(73) Assignee: Roche Palo Alto LLC, Palo Alto, CA (US)

( * ) Notice: Subject to any disclaimer, the term of this patent is extended or adjusted under 35 U.S.C. 154(b) by 569 days.

(21) Appl. No.: 10/997,170

(22) Filed: Nov. 24, 2004

(65) Prior Publication Data

US 2005/0113382 A1    May 26, 2005

Related U.S. Application Data

(60) Provisional application No. 60/524,547, filed on Nov. 24, 2003.

(51) Int. Cl.
*C07D 403/04* (2006.01)
*A61K 31/506* (2006.01)

(52) U.S. Cl. ........................ 514/256; 544/328
(58) Field of Classification Search ................ 544/328; 514/256

See application file for complete search history.

(56) References Cited

FOREIGN PATENT DOCUMENTS

| | | |
|---|---|---|
| EP | 0 168 262 A2 | 1/1986 |
| WO | WO 99/41253 A1 | 8/1999 |
| WO | WO 01/47921 A1 | 7/2001 |
| WO | WO 02/12198 A2 | 2/2002 |
| WO | WO 02/24681 * | 3/2002 |
| WO | WO 02/064096 A2 | 8/2002 |
| WO | WO 02/092090 A1 | 11/2002 |
| WO | WO 02/100838 A1 | 12/2002 |
| WO | WO 03/011836 A1 | 2/2003 |
| WO | WO 2004/072063 * | 8/2004 |
| WO | WO 2004/089286 A2 | 10/2004 |
| WO | WO 2005/009977 * | 2/2005 |
| WO | WO 2005/026129 * | 3/2005 |

OTHER PUBLICATIONS

Vippagunta et al., Crystalline Solids, Advanced Drug Delivery Reviews, 48, pp. 3-26, 2001.*
West, Solid Solutions, Solid State Chemistry and its applications, pp. 358 & 365, 1988.*
Ulrich, Chapter 4: Crystallization, Kirk-Othmer Encyclopedia of Chemical Technology, Aug. 2002.*
Bundgaard, Design of Prodrugs: Introduction, p. 1, 1985.*
Silverman, Prodrugs and Drug Delivery Systems, The Organic Chemistry of Drug Design and Drug Action, pp. 352-400, 1992.*
Mitchell, PubMed Abstract (Neurosci Biobehav Rev. 22(5):635-51) Sep. 1998.*

* cited by examiner

*Primary Examiner*—Deepak Rao
(74) *Attorney, Agent, or Firm*—Robert C. Hall

(57) ABSTRACT

Compounds of the formula (I):

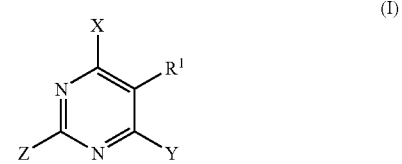

and pharmaceutically acceptable salts or prodrugs thereof, wherein X, Y, Z and $R^1$ are as defined herein. The invention also provides methods for preparing, compositions comprising, and methods for using compounds of formula I.

19 Claims, No Drawings

PYRAZOLYL AND IMIDAZOLYL PYRIMIDINES AS CRF ANTAGONISTS

CROSS REFERENCE TO RELATED APPLICATIONS

This application claims benefit under 35 U.S.C. 119(e) of U.S. Provisional Application No. 60/524,547 filed Nov. 24, 2003, which is hereby incorporated by reference in its entirety.

BACKGROUND OF THE INVENTION

Corticotropin releasing factor (CRF) or hormone (CRH) is one of several neurohormones synthesized by specific hypothalamic nuclei in the brain where it activates the transcription of the pro-opiomelanocortin (POMC) gene resulting in release of adrenocorticotropic hormone (ACTH) and beta-endorphin from anterior pituitary cells (Vale et al, *Science* 213, 1394-1397 (1981)). The fundamental role of CRF is to prepare the organism for an appropriate response to various stressors such as physical trauma, insults of the immune system and social interactions. CRF also has CNS effects by acting at higher centers in the brain, particularly cortical regions where there is a widespread distribution of CRF neurons. CRF is believed to be a key intermediary in communication between the immune, central nervous, endocrine and cardiovascular systems (Sapolsky et al, *Science* 238, 522-524 (1987)). The role played by CRF in integrating the response of the immune system to physiological, psychological and immunological stressors has been described in the art, e.g. J. E. Blalock, Physiological Reviews 69, 1 (1989) and J. E. Morley, *Life Sci.* 41, 527 (1987).

CRF antagonists are effective in the treatment of a wide range of stress-related illnesses, mood disorders such as depression, major depressive disorder, single episode depression, recurrent depression, child abuse induced depression, postpartum depression, dysthemia, bipolar disorder and cyclothymia; chronic fatigue syndrome; eating disorders such as obesity, anorexia and bulimia nervosa; generalized anxiety disorder; panic disorder; phobias; obsessive-compulsive disorder; post-traumatic stress disorder; pain perception such as fibromyalgia; headache; stress-induced gastrointestinal dysfunction such as irritable bowel syndrome (IBS), colonic hypersensitivity or spastic colon; hemorrhagic stress; ulcers; stress-induced psychotic episodes; inflammatory disorders such as rheumatoid arthritis and osteoarthritis; asthma; psoriasis; allergies; premature birth; hypertension; congestive heart failure; sleep disorders; neurodegenerative diseases such as Alzheimer's disease, senile dementia, Parkinson's disease and Huntington's disease; head or spinal cord trauma; ischemic neuronal damage; excitotoxic neuronal damage; epilepsy; stroke; psychosocial dwarfism; chemical dependencies and addictions; drug and alcohol withdrawal symptoms; stress-induced immune dysfunctions; immune suppression and stress-induced infections; cardiovascular or heart related diseases; fertility problems; and/or human immunodeficiency virus infections.

Accordingly clinical data suggests that CRF receptor antagonists may represent novel antidepressants and/or anxiolytic drugs that may be useful in the treatment of the neuropsychiatric disorders manifesting hypersecretion of CRF. Effective and specific antagonists of CRF are desired as potentially valuable therapeutic agents for the treatment of psychiatric disorders and neurological diseases.

SUMMARY OF THE INVENTION

The invention provides compounds of the formula (I):

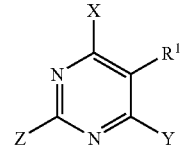

or pharmaceutically acceptable salts, solvates or prodrugs thereof, wherein:
X is optionally substituted heteroaryl;
Y is —$NR^aR^b$ wherein $R^a$ is hydrogen or alkyl and $R^b$ is aryl or heteroaryl;
Z is hydrogen or alkyl; and
$R^1$ is hydrogen, alkyl, alkoxy, haloalkyl, halo, hydroxy, cyano, nitro, —$NR^cR^d$, —$C(O)NR^cR^d$, alkylcarbonyl or alkylsulfonyl wherein $R^c$ and $R^d$ each independently is hydrogen or alkyl.

The invention also provides compositions comprising, methods for using, and methods for preparing the subject compounds.

DETAILED DESCRIPTION OF THE INVENTION

Definitions

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise.

"Agonist" refers to a compound that enhances the activity of another compound or receptor site.

"Alkyl" means the monovalent linear or branched saturated hydrocarbon moiety, consisting solely of carbon and hydrogen atoms, having from one to twelve carbon atoms. "Lower alkyl" refers to an alkyl group of one to six carbon atoms, i.e. $C_1$-$C_6$alkyl. Examples of alkyl groups include, but are not limited to, methyl, ethyl, propyl, isopropyl, isobutyl, sec-butyl, tert-butyl, pentyl, n-hexyl, octyl, dodecyl, and the like.

"Alkylene" means a linear saturated divalent hydrocarbon radical of one to six carbon atoms or a branched saturated divalent hydrocarbon radical of three to six carbon atoms, e.g., methylene, ethylene, 2,2-dimethylethylene, propylene, 2-methylpropylene, butylene, pentylene, and the like.

"Alkoxy" means a moiety of the formula —OR, wherein R is an alkyl moiety as defined herein. Examples of alkoxy moieties include, but are not limited to, methoxy, ethoxy, isopropoxy, and the like.

"Alkoxyalkyl" means a moiety of the formula —R'—R", where R' is alkylene and R" is alkoxy as defined herein.

"Alkylcarbonyl" means a moiety of the formula —R'—R", where R' is oxo and R" is alkyl as defined herein.

"Alkylsulfonyl" means a moiety of the formula —R'—R", where R' is —$SO_2$— and R" is alkyl as defined herein.

"Antagonist" refers to a compound that diminishes or prevents the action of another compound or receptor site.

"Aryl" means a monovalent cyclic aromatic hydrocarbon moiety consisting of a mono-, bi- or tricyclic aromatic ring. The aryl group can be optionally substituted as defined herein. Examples of aryl moieties include, but are not limited to, optionally substituted phenyl, naphthyl, phenanthryl, fluorenyl, indenyl, pentalenyl, azulenyl, oxydiphenyl, biphenyl, methylenediphenyl, aminodiphenyl, diphenylsulfidyl, diphenylsulfonyl, diphenylisopropylidenyl, benzodioxanyl, benzofuranyl, benzodioxylyl, benzopyranyl, benzoxazinyl, benzoxazinonyl, benzopiperadinyl, benzopiperazinyl, benzopyrrolidinyl, benzomorpholinyl, methylenedioxyphenyl, ethylenedioxyphenyl, and the like, including partially hydrogenated derivatives thereof.

"Arylalkyl" and "Aralkyl", which may be used interchangeably, mean a radical —$R^aR^b$ where $R^a$ is an alkylene group and $R^b$ is an aryl group as defined herein; e.g., phenylalkyls such as benzyl, phenylethyl, 3-(3-chlorophenyl)-2-methylpentyl, and the like are examples of arylalkyl.

"Cyanoalkyl" means a moiety of the formula —R'—R", where R' is alkylene as defined herein and R" is cyano or nitrile.

"Cycloalkyl" means a monovalent saturated carbocyclic moiety consisting of mono- or bicyclic rings. Cycloalkyl can optionally be substituted with one or more substituents, wherein each substituent is independently hydroxy, alkyl, alkoxy, halo, haloalkyl, amino, monoalkylamino, or dialkylamino, unless otherwise specifically indicated. Examples of cycloalkyl moieties include, but are not limited to, cyclopropyl, cyclobutyl, cyclopentyl, cyclohexyl, cycloheptyl, and the like, including partially unsaturated derivatives thereof.

"Cycloalkylalkyl" means a moiety of the formula —R'—R", where R' is alkylene and R" is cycloalkyl as defined herein.

"Heteroalkyl" means an alkyl radical as defined herein wherein one, two or three hydrogen atoms have been replaced with a substituent independently selected from the group consisting of —$OR^a$, —$NR^bR^c$, and —$S(O)R^d$ (where n is an integer from 0 to 2), with the understanding that the point of attachment of the heteroalkyl radical is through a carbon atom, wherein $R^a$ is hydrogen, acyl, alkyl, cycloalkyl, or cycloalkylalkyl; $R^b$ and $R^c$ are independently of each other hydrogen, acyl, alkyl, cycloalkyl, or cycloalkylalkyl; and when n is 0, $R^d$ is hydrogen, alkyl, cycloalkyl, or cycloalkylalkyl, and when n is 1 or 2, $R^d$ is alkyl, cycloalkyl, cycloalkylalkyl, amino, acylamino, monoalkylamino, or dialkylamino. Representative examples include, but are not limited to, 2-hydroxyethyl, 3-hydroxypropyl, 2-hydroxy-1-hydroxymethylethyl, 2,3-dihydroxypropyl, 1-hydroxymethylethyl, 3-hydroxybutyl, 2,3-dihydroxybutyl, 2-hydroxy-1-methylpropyl, 2-aminoethyl, 3-aminopropyl, 2-methylsulfonylethyl, aminosulfonylmethyl, aminosulfonylethyl, aminosulfonylpropyl, methylaminosulfonylmethyl, methylaminosulfonylethyl, methylaminosulfonylpropyl, and the like.

"Heteroaryl" means a monocyclic or bicyclic radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring may be optionally substituted as defined herein. Examples of heteroaryl moieties include, but are not limited to, optionally substituted imidazolyl, oxazolyl, isoxazolyl, thiazolyl, isothiazolyl, oxadiazolyl, thiadiazolyl, pyrazinyl, thienyl, benzothienyl, thiophenyl, furanyl, pyranyl, pyridyl, pyrrolyl, pyrazolyl, pyrimidyl, quinolinyl, isoquinolinyl, benzofuryl, benzothiophenyl, benzothiopyranyl, benzimidazolyl, benzooxazolyl, benzooxadiazolyl, benzothiazolyl, benzothiadiazolyl, benzopyranyl, indolyl, isoindolyl, triazolyl, triazinyl, quinoxalinyl, purinyl, quinazolinyl, quinolizinyl, naphthyridinyl, pteridinyl, carbazolyl, azepinyl, diazepinyl, acridinyl and the like, including partially hydrogenated derivatives thereof.

The terms "halo" and "halogen", which may be used interchangeably, refer to a substituent fluoro, chloro, bromo, or iodo.

"Haloalkyl" means alkyl as defined herein in which one or more hydrogen has been replaced with same or different halogen. Exemplary haloalkyls include —$CH_2Cl$, —$CH_2CF_3$, —$CH_2CCl_3$, perfluoroalkyl (e.g., —CF3), and the like.

"Heterocycloamino" means a saturated ring wherein at least one ring atom is N, NH or N-alkyl and the remaining ring atoms form an alkylene group.

"Heterocyclyl" means a monovalent saturated moiety, consisting of one to three rings, incorporating one, two, or three or four heteroatoms (chosen from nitrogen, oxygen or sulfur). The heterocyclyl ring may be optionally substituted as defined herein. Examples of heterocyclyl moieties include, but are not limited to, optionally substituted piperidinyl, piperazinyl, homopiperazinyl, azepinyl, pyrrolidinyl, pyrazolidinyl, imidazolinyl, imidazolidinyl, pyridinyl, pyridazinyl, pyrimidinyl, oxazolidinyl, isoxazolidinyl, morpholinyl, thiazolidinyl, isothiazolidinyl, quinuclidinyl, quinolinyl, isoquinolinyl, benzimidazolyl, thiadiazolylidinyl, benzothiazolidinyl, benzoazolylidinyl, dihydrofuryl, tetrahydrofuryl, dihydropyranyl, tetrahydropyranyl, thiamorpholinyl, thiamorpholinylsulfoxide, thiamorpholinylsulfone, dihydroquinolinyl, dihydrisoquinolinyl, tetrahydroquinolinyl, tetrahydrisoquinolinyl, and the like.

"Optionally substituted", when used in association with "aryl", phenyl", "heteroaryl" or "heterocyclyl", means an aryl, phenyl, heteroaryl or heterocyclyl which is optionally substituted independently with one to four substituents, preferably one or two substituents selected from alkyl, cycloalkyl, cycloalkylalkyl, heteroalkyl, hydroxyalkyl, halo, nitro, cyano, hydroxy, alkoxy, amino, acylamino, mono-alkylamino, di-alkylamino, haloalkyl, haloalkoxy, heteroalkyl, —COR (where R is hydrogen, alkyl, phenyl or phenylalkyl), —(CR'R")$_n$—COOR (where n is an integer from 0 to 5, R' and R" are independently hydrogen or alkyl, and R is hydrogen, alkyl, cycloalkyl, cycloalkylalkyl, phenyl or phenylalkyl), or —(CR'R")$_n$—CONR$^a$R$^b$ (where n is an integer from 0 to 5, R' and R" are independently hydrogen or alkyl, and $R^a$ and $R^b$ are, independently of each other, hydrogen, alkyl, cycloalkyl, cycloalkylalkyl, phenyl or phenylalkyl).

"Leaving group" means the group with the meaning conventionally associated with it in synthetic organic chemistry, i.e., an atom or group displaceable under substitution reaction conditions. Examples of leaving groups include, but are not limited to, halogen, alkane- or arylenesulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, acyloxy, and the like.

"Modulator" means a molecule that interacts with a target. The interactions include, but are not limited to, agonist, antagonist, and the like, as defined herein.

"Optional" or "optionally" means that the subsequently described event or circumstance may but need not occur, and that the description includes instances where the event or circumstance occurs and instances in which it does not.

"Disease state" means any disease, condition, symptom, or indication.

"Inert organic solvent" or "inert solvent" means the solvent is inert under the conditions of the reaction being described in conjunction therewith, including for example, benzene, toluene, acetonitrile, tetrahydrofuran, N,N-dimethylformamide, chloroform, methylene chloride or dichloromethane, dichloroethane, diethyl ether, ethyl acetate, acetone, methyl ethyl ketone, methanol, ethanol, propanol, isopropanol, tert-butanol, dioxane, pyridine, and the like. Unless specified to the contrary, the solvents used in the reactions of the present invention are inert solvents.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

"Pharmaceutically acceptable salts" of a compound means salts that are pharmaceutically acceptable, as defined herein, and that possess the desired pharmacological activity of the parent compound. Such salts include:

acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic, camphorsulfonic acid, citric acid, ethanesulfonic acid, flimaric acid, glucoheptonic acid, gluconic acid, glutamic acid, glycolic acid, hydroxynaphtoic acid, 2-hydroxyethanesulfonic acid, lactic acid, maleic acid, malic acid, malonic acid, mandelic acid, methanesulfonic acid, muconic acid, 2-naphthalenesulfonic acid, propionic acid, salicylic acid, succinic acid, tartaric acid, p-toluenesulfonic acid, trimethylacetic acid, and the like; or salts formed when an acidic proton present in the parent compound either is replaced by a metal ion, e.g., an alkali metal ion, an alkaline earth ion, or an aluminum ion; or coordinates with an organic or inorganic base. Acceptable organic bases include diethanolamine, ethanolamine, N-methylglucamine, triethanolamine, tromethamine, and the like. Acceptable inorganic bases include aluminum hydroxide, calcium hydroxide, potassium hydroxide, sodium carbonate and sodium hydroxide.

The preferred pharmaceutically acceptable salts are the salts formed from acetic acid, hydrochloric acid, sulphuric acid, methanesulfonic acid, maleic acid, phosphoric acid, tartaric acid, citric acid, sodium, potassium, calcium, zinc, and magnesium.

It should be understood that all references to pharmaceutically acceptable salts include solvent addition forms (solvates) or crystal forms (polymorphs) as defined herein, of the same acid addition salt.

The terms "pro-drug" and "prodrug", which may be used interchangeably herein, refer to any compound which releases an active parent drug according to formula I in vivo when such prodrug is administered to a mammalian subject. Prodrugs of a compound of formula I are prepared by modifying one or more functional group(s) present in the compound of formula I in such a way that the modification(s) may be cleaved in vivo to release the parent compound. Prodrugs include compounds of formula I wherein a hydroxy, amino, or sulfhydryl group in a compound of Formula I is bonded to any group that may be cleaved in vivo to regenerate the free hydroxyl, amino, or sulfhydryl group, respectively. Examples of prodrugs include, but are not limited to, esters (e.g., acetate, formate, and benzoate derivatives), carbamates (e.g., N,N-dimethylaminocarbonyl) of hydroxy functional groups in compounds of formula I, N-acyl derivatives (e.g. N-acetyl) N-Mannich bases, Schiff bases and enaminones of amino functional groups, oximes, acetals, ketals and enol esters of ketone and aldehyde functional groups in compounds of Formula I, and the like, see Bundegaard, H. "Design of Prodrugs" p1-92, Elesevier, New York-Oxford (1985), and the like.

"Protective group" or "protecting group" means the group which selectively blocks one reactive site in a multifunctional compound such that a chemical reaction can be carried out selectively at another unprotected reactive site in the meaning conventionally associated with it in synthetic chemistry. Certain processes of this invention rely upon the protective groups to block reactive nitrogen and/or oxygen atoms present in the reactants. For example, the terms "amino-protecting group" and "nitrogen protecting group" are used interchangeably herein and refer to those organic groups intended to protect the nitrogen atom against undesirable reactions during synthetic procedures. Exemplary nitrogen protecting groups include, but are not limited to, trifluoroacetyl, acetamido, benzyl (Bn), benzyloxycarbonyl (carbobenzyloxy, CBZ), p-methoxybenzyloxycarbonyl, p-nitrobenzyloxycarbonyl, tert-butoxycarbonyl (BOC), and the like. The artisan in the art will know how to chose a group for the ease of removal and for the ability to withstand the following reactions.

"Solvates" means solvent additions forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

"Subject" means mammals and non-mammals. Mammals means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgement of the attending medical or veterinary practitioner, and other factors.

The terms "those defined above" and "those defined herein" when referring to a variable incorporates by reference the broad definition of the variable as well as preferred, more preferred and most preferred definitions, if any.

"Treating" or "treatment" of a disease state includes:
(i) preventing the disease state, i.e. causing the clinical symptoms of the disease state not to develop in a subject that may be exposed to or predisposed to the disease state, but does not yet experience or display symptoms of the disease state.
(ii) inhibiting the disease state, i.e., arresting the development of the disease state or its clinical symptoms, or
(iii) relieving the disease state, i.e., causing temporary or permanent regression of the disease state or its clinical symptoms.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

"Mood disorders" or "affective disorders" means psychopathologic conditions in which a pervasive disturbance of mood constitutes the core manifestation. These terms subsume anxiety and related neuroses, especially the depressive form. Examples of "mood disorders" or "affective disorders" include, but are not limited to, depression, major depressive disorder, single episode depression, recurrent depression, child abuse induced depression, postpartum depression, dysthemia, unipolar disorder, bipolar disorder with manifestations of insomnia and eating disorder, dysthymic disorder, double depression, morbid and clinical depression, mania and cyclothymia.

Nomenclature

In general, the nomenclature used in this Application is based on AUTONOM™ v.4.0, a Beilstein Institute computerized system for the generation of IUPAC systematic nomenclature. For convenience, the IUPAC numbering of the positions of representative pyrimidine compounds described herein are shown by the formula:

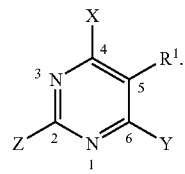

Chemical structures shown herein were prepared using ISIS® version 2.2. Any open valency appearing on a carbon, oxygen or nitrogen atom in the structures herein indicates the presence of a hydrogen.

All patents and publications identified herein are incorporated herein by reference in their entirety.

COMPOUNDS OF THE INVENTION

The invention provides compounds of the formula (I):

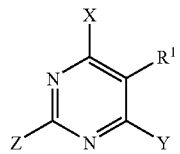

(I)

or pharmaceutically acceptable salts, solvates or prodrugs thereof, wherein:
  X is an optionally substituted heteroaryl;
  Y is —NR$^a$R$^b$ wherein R$^a$ is hydrogen or alkyl and R$^b$ is aryl or heteroaryl;
  Z is hydrogen or alkyl; and
  R$^1$ is hydrogen, alkyl, alkoxy, haloalkyl, halo, hydroxy, cyano, nitro, —NR$^c$R$^d$, —C(O)NR$^c$R$^d$, alkylcarbonyl or alkylsulfonyl wherein R$^c$ and R$^d$ each independently is hydrogen or alkyl.

By way of example, and not of limitation, X may in certain embodiments comprise an optionally substituted heteroaryl selected from pyrazolyl, imidazolyl, pyrrolyl, pyridyl, pyridazyl and pyrimidyl. In many embodiments X may be an optionally substituted pyrazolyl, optionally substituted imidazolyl or optionally substituted pyrrolyl. In many embodiments Z may be alkyl and R$^a$ may be hydrogen.

In certain embodiments, X may be an optionally substituted pyrazol-1-yl such as 3-methylpyrazol-1-yl, 3,5-dimethylpyrazol-1-yl, 4-chloro-3,5-dimethylpyrazol-1-yl, 3-propylpyrazol-1-yl, or 3-butyl-4-propylpyrazol-1-yl. In other embodiments X may be an optionally substituted imidazol-1-yl such as 2-methylimidazol-1-yl, 4-methylimidazol-1-yl or 4-phenylimidazol-1-yl.

In certain embodiments R$^b$ may be an optionally substituted phenyl such as 2,4,6-trichlorophenyl. In other embodiments R$^b$ may be an optionally substituted heteroaryl such as a pyridinyl, pyrimidinyl or thienyl. R$^1$ may, in many embodiments, be hydrogen, alkyl or halo.

In certain embodiments, the subject compounds may be more specifically of the formula (II)

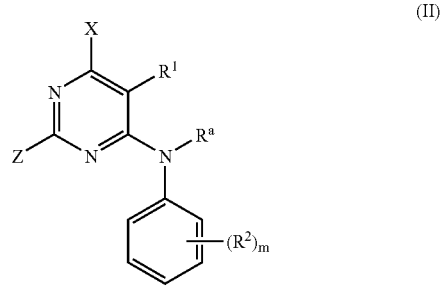

(II)

wherein:
  m is from 0 to 4;
  X is optionally substituted pyrazolyl or optionally substituted imidazolyl;
  Z is alkyl;
  each R$^2$ independently is hydrogen, alkyl, alkoxy, haloalkyl, halo, hydroxyl, cyano, nitro, —NR$^c$R$^d$, —C(O)NR$^c$R$^d$, alkylcarbonyl or alkylsulfonyl;
  R$^1$, R$^a$, R$^c$ and R$^d$ are as defined herein.

In some embodiments of formula (II), X may be 3-methylpyrazol-1-yl, 3,5-dimethylpyrazol-1-yl, 4-chloro-3,5-dimethylpyrazol-1-yl, 3-propylpyrazol-1-yl, or 3-butyl-4-propylpyrazol-1-yl. In other embodiments of formula (II), X may be 2-methylimidazol-1-yl, 4-methylimidazol-1-yl or 4-phenylimidazol-1-yl.

In certain embodiments, the compounds of formula (II) may be more specifically of the formula (III)

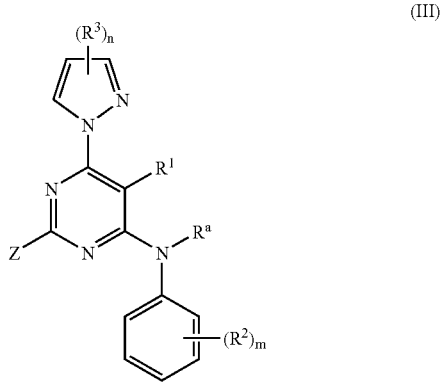

(III)

wherein:
  m is from 0 to 4;
  n is from 0 to 3;

each $R^2$ independently is hydrogen, alkyl, alkoxy, haloalkyl, halo, hydroxyl, cyano, nitro, —$NR^cR^d$, —$C(O)NR^cR^d$, alkylcarbonyl or alkylsulfonyl;

Z is alkyl;

each $R^3$ independently is alkyl, optionally substituted phenyl or halo; and $R^1$, $R^a$, $R^c$ and $R^d$ are as defined herein.

In certain embodiments of formula (III), n may be 1 or 2. In some embodiments, m may be 3, $R^2$ may be halo, and $R^1$ may be hydrogen, alkyl or halo. In specific embodiments, n may is 1 and $R^3$ is methyl or propyl. In still other embodiments n is 2, one of $R^3$ is propyl, and the other $R^3$ is butyl.

In certain embodiments, the compounds of formula (II) may be more specifically of the formula (IV)

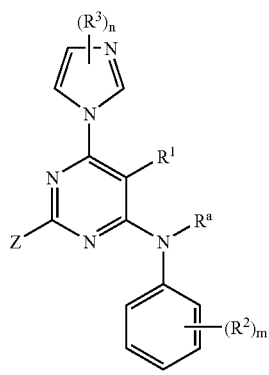

(IV)

wherein:

m is from 0 to 4;

n is from 0 to 3;

each $R^2$ independently is hydrogen, alkyl, alkoxy, haloalkyl, halo, hydroxyl, cyano, nitro, —$NR^cR^d$, —$C(O)NR^cR^d$, alkylcarbonyl or alkylsulfonyl;

Z is alkyl;

each $R^3$ independently is alkyl, optionally substituted phenyl or halo; and $R^1$, $R^a$, $R^c$ and $R^d$ are as defined herein.

In certain embodiments of formula (IV), n is 1 and $R^3$ is methyl or phenyl, and $R^1$ may be hydrogen, alkyl or halo. In specific embodiments, m is 3 and $R^2$ is halo.

It is to be understood that the scope of this invention encompasses not only the various isomers which may exist but also the various mixture of isomers which may be formed. Furthermore, the scope of the present invention also encompasses solvates and salts of Compounds of Formula I.

In embodiments where any of $R^1$, $R^2$, $R^3$, $R^a$, $R^b$, $R^c$, and $R^d$ are alkyl or otherwise include an alkyl moiety, the alkyl may be lower alkyl such as $C_1$-$C_6$alkyl, and more specifically $C_1$-$C_4$alkyl.

Representative compounds in accordance with the invention are shown in Table 1. Unless indicated otherwise, the compounds of Table 1 were isolated as hydrochloride salts according the experimental procedures described below.

TABLE 1

| | Name (Autonom ®) | Structure | Mp, ° C. or (M+H) |
|---|---|---|---|
| 1 | [2-Methyl-6-(3-methyl-pyrazol-1-yl)-pyrimidin-4-yl]-(2,4,6-trichloro-phenyl)-amine | 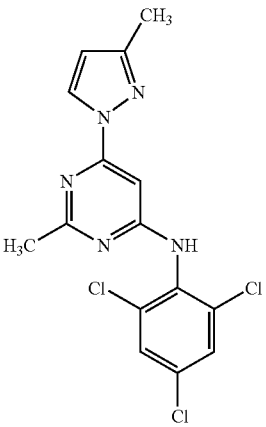 | 245-247° |

TABLE 1-continued

| Name (Autonom ®) | Structure | Mp, ° C. or (M+H) |
|---|---|---|
| 2 [6-(3,5-Dimethyl-pyrazol-1-yl)-2-methyl-pyrimidin-4-yl]-(2,4,6-trichloro-phenyl)-amine | | 235-237° |
| 3 [6-(4-Chloro-3,5-dimethyl-pyrazol-1-yl)-2-methyl-pyrimidin-4-yl]-(2,4,6-trichloro-phenyl)-amine | | 418 |
| 4 [2-Methyl-6-(3-propyl-pyrazol-1-yl)-pyrimidin-4-yl]-(2,4,6-trichloro-phenyl)-amine | | 398 |

TABLE 1-continued
| | Name (Autonom ®) | Structure | Mp, ° C. or (M+H) |
|---|---|---|---|
| 5 | [5-Chloro-2-methyl-6-(3-methyl-pyrazol-1-yl)-pyrimidin-4-yl]-(2,4,6-trichloro-phenyl)-amine | 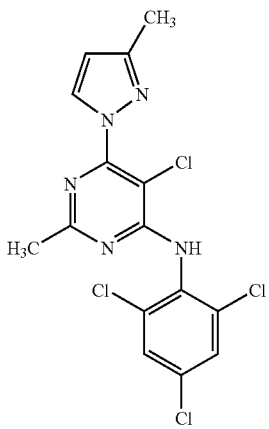 | 118-121° |
| 6 | [2,5-Dimethyl-6-(3-propyl-pyrazol-1-yl)-pyrimidin-4-yl]-(2,4,6-trichloro-phenyl)-amine | 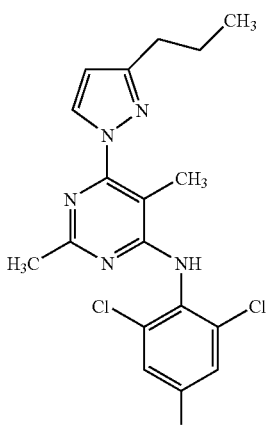 | 169-170° |
| 7 | [6-(3-Butyl-4-propyl-pyrazol-1-yl)-2,5-dimethyl-pyrimidin-4-yl]-(2,4,6-trichloro-phenyl)-amine | 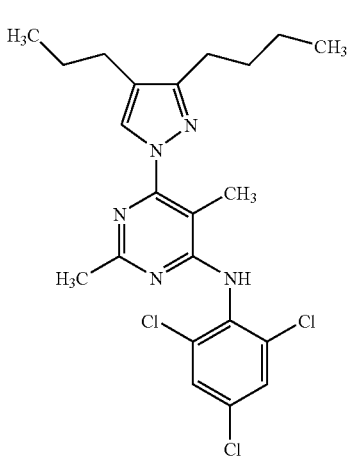 | 139-148° |

TABLE 1-continued

| | Name (Autonom ®) | Structure | Mp, ° C. or (M+H) |
|---|---|---|---|
| 8 | [6-(3-Butyl-4-propyl-pyrazol-1-yl)-5-chloro-2-methyl-pyrimidin-4-yl]-(2,4,6-trichloro-phenyl)-amine | 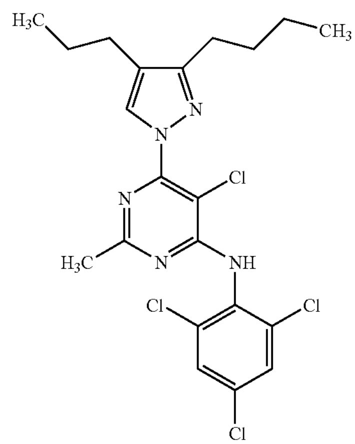 | 99-110° |
| 9 | [2-Methyl-6-(2-methyl-imidazol-1-yl)-pyrimidin-4-yl]-(2,4,6-trichloro-phenyl)-amine | 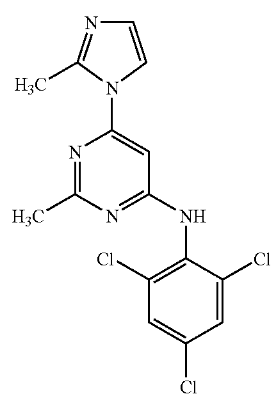 | 177-179° |
| 10 | [2-Methyl-6-(4-phenyl-imidazol-1-yl)-pyrimidin-4-yl]-(2,4,6-trichloro-phenyl)-amine | 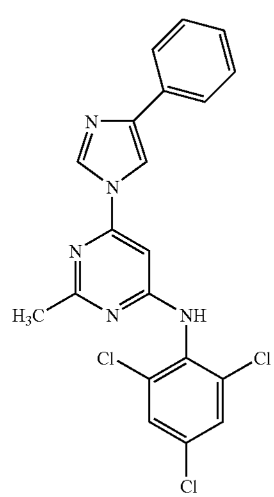 | 235-238° |

TABLE 1-continued
| | Name (Autonom ®) | Structure | Mp, ° C. or (M+H) |
|---|---|---|---|
| 11 | [2-Methyl-6-(4-methyl-imidazol-1-yl)-pyrimidin-4-yl]-(2,4,6-trichloro-phenyl)-amine | 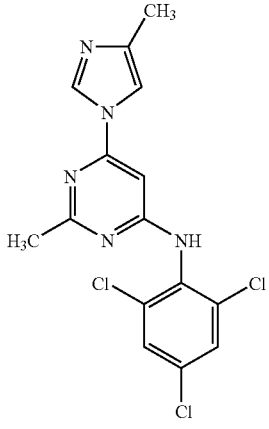 | 168-174° |
| 12 | [5-Chloro-2-methyl-6-(4-methyl-imidazol-1-yl)-pyrimidin-4-yl]-(2,4,6-trichloro-phenyl)-amine | 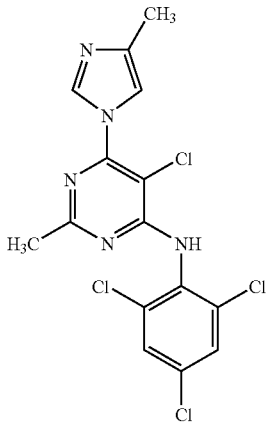 | 184-186° |
| 13 | [5-Chloro-6-(4-chloro-3,5-dimethyl-pyrazol-1-yl)-2-methyl-pyrimidin-4-yl]-(2,4,6-trichloro-phenyl)-amine | 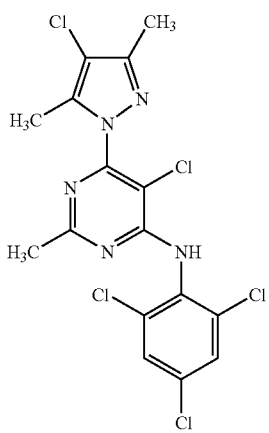 | 453 |

TABLE 1-continued

| Name (Autonom ®) | Structure | Mp, ° C. or (M+H) |
|---|---|---|
| 14 (2,4-Dimethyl-phenyl)-[2-methyl-6-(3-propyl-pyrazol-1-yl)-pyrimidin-4-yl]-amine | | 114-119° |

Another aspect of the invention provides a composition comprising a therapeutically effective amount of at least one compound of formula (I) together with a pharmaceutically acceptable carrier.

Yet another aspect of the invention provides method for treating a subject having a disease state that is alleviated by treatment with a CRF receptor antagonist, comprising administering to such a subject a therapeutically effective amount of a compound of formula I. The disease state may comprise, for example, phobias, stress-related illnesses, mood disorders, eating disorders, generalized anxiety disorders, stress-induced gastrointestinal dysfunctions, neurodegenerative diseases, and neuropsychiatric disorders.

Another aspect of the present invention provides a method for producing a compound of formula I.

Synthesis

Compounds of the present invention can be made by a variety of methods depicted in the illustrative synthetic reaction schemes shown and described below.

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis;* Wiley & Sons: New York, 1991, Volumes 1-15; *Rodd's Chemistry of Carbon Compounds,* Elsevier Science Publishers, 1989, Volumes 1-5 and Supplementals; and *Organic Reactions,* Wiley & Sons: New York, 1991, Volumes 1-40. The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

Scheme A below illustrates one synthetic procedure usable to prepare specific compounds of formula (II) wherein L is a leaving group such as a halogen and may the same or different in each occurrence, and X, m, $R^1$ and $R^3$ are as defined herein.

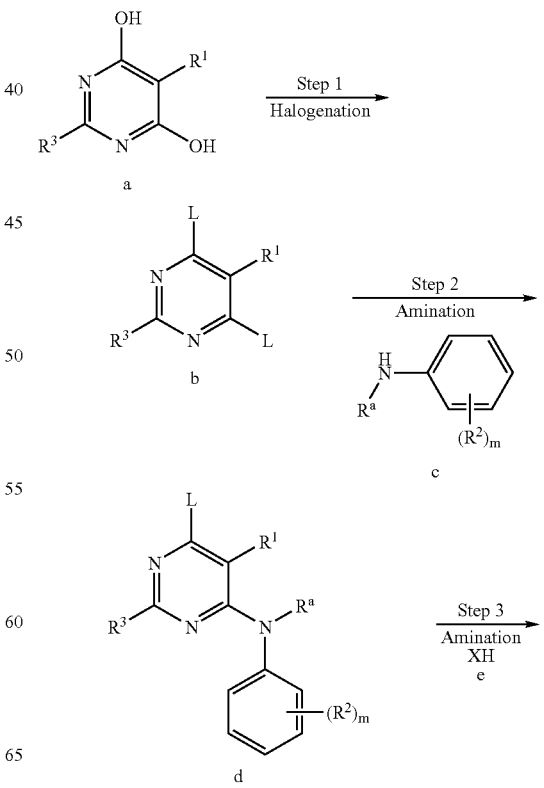

-continued

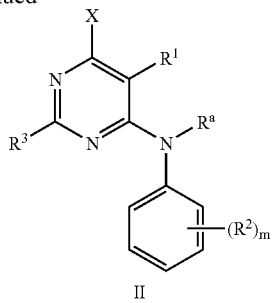

II

In step 1 of Scheme A, halogenation of dihydroxypyrimidine a provides dihalopyrimidine b. Various dihydroxypyrimidines a are commercially available or readily prepared via well-known procedures, and may be used in this step. This step may be carried out using $POCl_3$, $POBr_3$ or like reagent. An amine base may be present during the reaction.

In step 2, a first amination occurs by reaction of aniline c with dihalopyrimidine b to afford aminopyrimidine d. Numerous anilines c are commercially available or easily prepared by techniques well-known in the art, and may be used in this step. The alkylation of step 2 may be effected in the presence of a strong base such as NaH with heating under polar aprotic solvent conditions.

In step 3, a second amination is carried out by reaction of aminopyrimidine d with a secondary amine e to yield a pyridine compound of formula (II) in accordance with the invention. This reaction may be effected in the presence of acid under polar aprotic solvent conditions. Secondary amine e may comprise, for example, a heteroaryl amine such as a pyrazole, imidazole, pyrrole, or the like, which may optionally be substituted.

Many variations on the procedure of Scheme A are possible and will suggest themselves to those skilled in the art. For example, in step 2 aniline c may be replaced with an aminopyridine, aminopyrimidine, aminothiene, or other heteroarylamine.

Specific details for producing compounds of formula (II) are described in the Examples section below.

Utility

The compounds of the invention are usable for the treatment of a wide range of stress-related illnesses, mood disorders such as depression, major depressive disorder, single episode depression, recurrent depression, child abuse induced depression, postpartum depression, dysthemia, bipolar disorder and cyclothymia; chronic fatigue syndrome; eating disorders such as obesity, anorexia and bulimia nervosa; generalized anxiety disorder; panic disorder; phobias; obsessive-compulsive disorder; post-traumatic stress disorder; pain perception such as fibromyalgia; headache; stress-induced gastrointestinal dysfunction such as irritable bowel syndrome (IBS), colonic hypersensitivity or spastic colon; hemorrhagic stress; ulcers; stress-induced psychotic episodes; inflammatory disorders such as rheumatoid arthritis and osteoarthritis; asthma; psoriasis; allergies; premature birth; hypertension; congestive heart failure; sleep disorders; neurodegenerative diseases such as Alzheimer's disease, senile dementia, Parkinson's disease and Huntington's disease; head or spinal cord trauma; ischemic neuronal damage; excitotoxic neuronal damage; epilepsy; stroke; psychosocial dwarfism; chemical dependencies and addictions; drug and alcohol withdrawal symptoms; stress-induced immune dysfunctions; immune suppression and stress-induced infections; cardiovascular or heart related diseases; fertility problems; and/or human immunodeficiency virus infections. Accordingly clinical data suggests that CRF receptor antagonists may represent novel antidepressants and/or anxiolytic drugs that may be useful in the treatment of the neuropsychiatric disorders manifesting hypersecretion of CRF.

Administration and Pharmaceutical Composition

The invention includes pharmaceutical compositions comprising at least one compound of the present invention, or an individual isomer, racemic or non-racemic mixture of isomers or a pharmaceutically acceptable salt or solvate thereof, together with at least one pharmaceutically acceptable carrier, and optionally other therapeutic and/or prophylactic ingredients.

In general, the compounds of the invention will be administered in a therapeutically effective amount by any of the accepted modes of administration for agents that serve similar utilities. Suitable dosage ranges are typically 1-500 mg daily, preferably 1-100 mg daily, and most preferably 1-30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this Application, to ascertain a therapeutically effective amount of the compounds of the present invention for a given disease.

Compounds of the invention may be administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. The preferred manner of administration is generally oral using a convenient daily dosage regimen which can be adjusted according to the degree of affliction.

A compound or compounds of the invention, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

The compounds of the invention may be formulated in a wide variety of oral administration dosage forms. The pharmaceutical compositions and dosage forms may comprise a compound or compounds of the present invention or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavouring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatine, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile, pyrogen-free water.

The compounds of the invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatine and glycerine or sucrose and acacia; and mouthwashes comprising the active ingredient in a suitable liquid carrier.

The compounds of the invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the invention may be formulated for vaginal administration. Pessaries, tampons, creams, gels, pastes, foams or sprays containing in addition to the active ingredient such carriers as are known in the art to be appropriate.

The subject compounds may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatine or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylazacycloheptan-2-one). Sustained release delivery systems are inserted subcutaneously into the subdermal layer by surgery or injection. The subdermal implants encapsulate the compound in a lipid soluble membrane, e.g., silicone rubber, or a biodegradable polymer, e.g., polylactic acid.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in *Remington: The Science and Practice of Pharmacy* 1995, edited by E. W. Martin, Mack Publishing Company, 19th edition, Easton, Pa. Representative pharmaceutical formulations containing a compound of the present invention are described in Examples 6-12.

EXAMPLES

The following preparations and examples are given to enable those skilled in the art to more clearly understand and to practice the present invention. They should not be considered as limiting the scope of the invention, but merely as being illustrative and representative thereof.

Example 1

[2-Methyl-6-(3-methyl-pyrazol-1-yl)-pyrimidin-4-yl]-(2,4,6-trichloro-phenyl)-amine

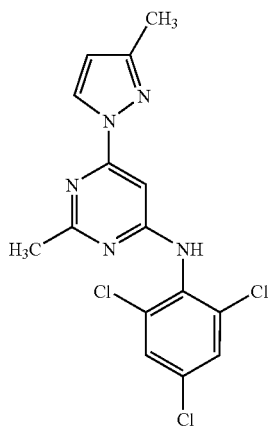

The compound [2-Methyl-6-(3-methyl-pyrazol-1-yl)-pyrimidin-4-yl]-(2,4,6-trichloro-phenyl)-amine was prepared in this example according to the procedure of Scheme B.

SCHEME B

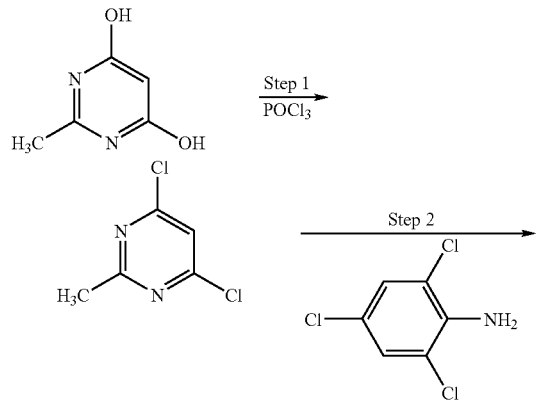

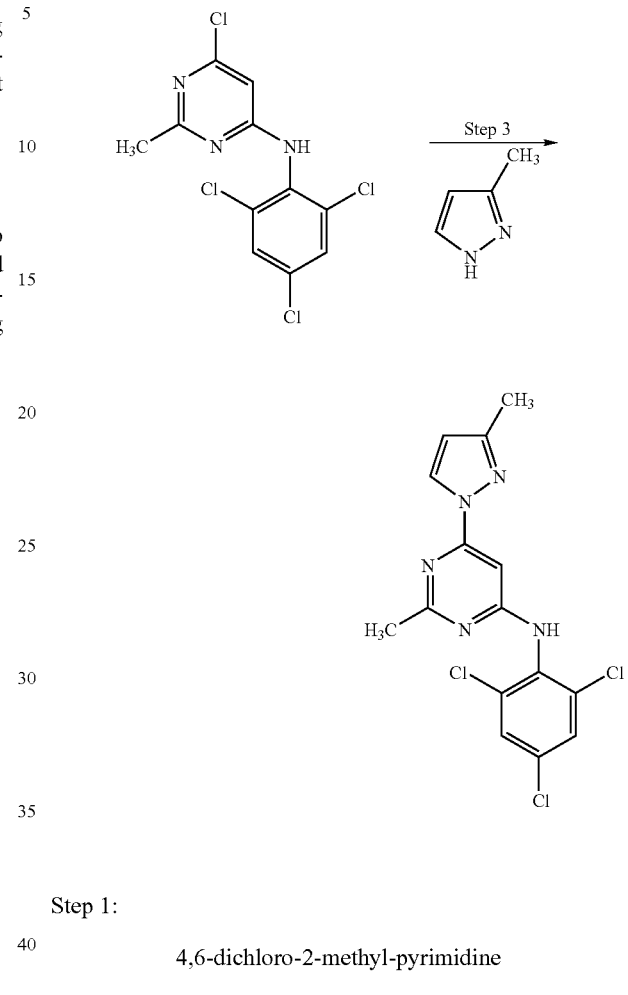

Step 1:

4,6-dichloro-2-methyl-pyrimidine

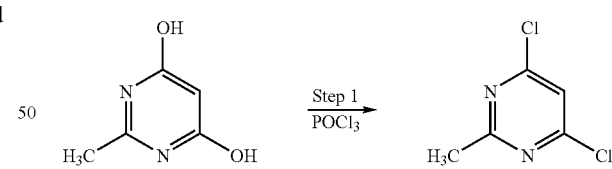

To a stirred suspension of 2-methyl-pyrimidine-4,6-diol (10.0 g, 79.4 mmol) in phosphorous oxychloride (75 mL) was added N,N-diethylaniline (5 mL). This mixture was heated under reflux for two hours and then cooled to room temperature, after which the remaining phosphorous oxychloride was removed in vacuo. The residue was carefully diluted with cold water, extracted three times with 150 mL of diethyl ether, and the combined ether layers were dried on potassium carbonate. The solvent was removed in vacuo to yield an oil that solidified under vacuum to form a light yellow solid, 4.68 g (36%) of 4,6-dichloro-2-methyl-pyrimidine; ms (M+H) 164.

Step 2:

(6-Chloro-2-methyl-pyrimidin-4-yl)-(2,4,6-trichloro-phenyl)-amine

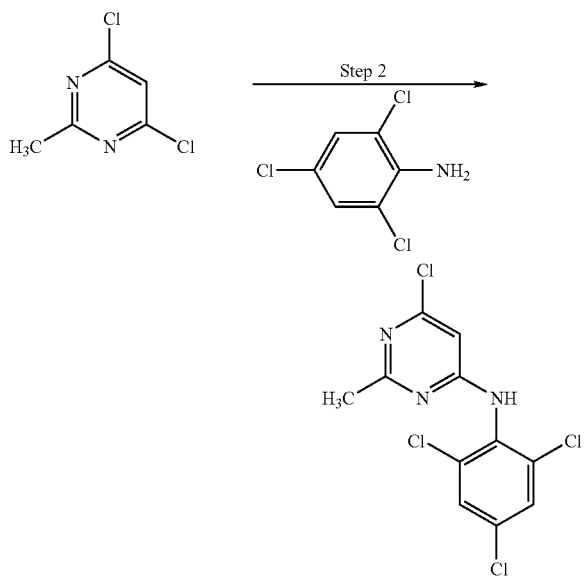

To a solution of 4,6-dichloro-2-methyl-pyrimidine (4.68 g, 28.7 mmol) in 70 mL of dry THF at room temperature under nitrogen was added sodium hydride (2.29 g, 57.4 mmol). The suspension was stirred under nitrogen at room temperature for 15 minutes, after which 2,4,6-trichloro-phenylamine (4.68 g, 28.8 mmol) was added in portions. The resulting mixture was refluxed under nitrogen for 3 hours, then cooled and quenched by addition of water (300 mL) and extracted three times with 100 mL of ethyl acetate. The combined organic layers were dried on potassium carbonate, and then evaporated to dryness in vacuo to yield a solid which was recrystallized from diethyl ether—hexanes to provide 6.75 g (73%) of 6-chloro-2-methyl-pyrimidin-4-yl)-(2,4,6-trichloro-phenyl)-amine; ms (M+H) 324.

Step 3:

[2-Methyl-6-(3-methyl-pyrazol-1-yl)-pyrimidin-4-yl]-(2,4,6-trichloro-phenyl)-amine

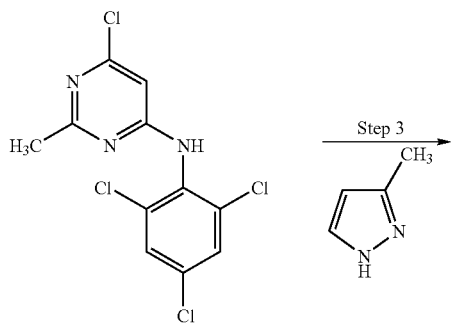

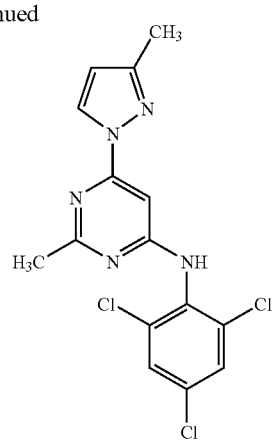

6-Chloro-2-methyl-pyrimidin-4-yl)-(2,4,6-trichloro-phenyl)-amine (0.5 g, 1.5 mmol), 3-methyl pyrazole (0.15 g, 1.86 mmol) and 2 mL of diglyme (diethylene glycol dimethyl ether) were added to a reaction vial. The reaction vial was sealed and heated to approximately 180°-190° for 2 hours and forty minutes. The vial was cooled, and the contents were quenched by addition to 50 mL of water, which was then extracted three times with 50 mL of ethyl acetate. The combined organic layers were washed with brine, dried over sodium sulfate, and evaporated under vacuum yielded a solid that was recrystallized from diethyl ether—hexanes to afford 116 mg (36%) of [2-methyl-6-(3-methyl-pyrazol-1-yl)-pyrimidin-4-yl]-(2,4,6-trichloro-phenyl)-amine: mp 245-247°; ms (M+H) 370.

Using the above procedure with the appropriate dihydroxy pyriridines in step 1, anilines in step 2, and heteroaryl amines in step 3, provided several additional compounds which are shown in Table 1.

Example 2

Formulations

Pharmaceutical preparations for delivery by various routes are formulated as shown in the following Tables. "Active ingredient" or "Active compound" as used in the Tables means one or more of the Compounds of Formula I.

| Composition for Oral Administration | |
|---|---|
| Ingredient | % wt./wt. |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

| Composition for Oral Administration | |
|---|---|
| Ingredient | % wt./wt. |
| Active ingredient | 20.0% |
| Magnesium stearate | 0.5% |

Composition for Oral Administration

| Ingredient | % wt./wt. |
| --- | --- |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

Composition for Oral Administration

| Ingredient | Amount |
| --- | --- |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

Parenteral Formulation

| Ingredient | % wt./wt. |
| --- | --- |
| Active ingredient | 0.25 g |
| Sodium Chloride | qs to make isotonic |
| Water for injection | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

Suppository Formulation

| Ingredient | % wt./wt. |
| --- | --- |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

Topical Formulation

| Ingredients | grams |
| --- | --- |
| Active compound | 0.2-2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

Nasal Spray Formulations

Several aqueous suspensions containing from about 0.025-0.5 percent active compound are prepared as nasal spray formulations. The formulations optionally contain inactive ingredients such as, for example, microcrystalline cellulose, sodium carboxymethylcellulose, dextrose, and the like. Hydrochloric acid may be added to adjust pH. The nasal spray formulations may be delivered via a nasal spray metered pump typically delivering about 50-100 microliters of formulation per actuation. A typical dosing schedule is 2-4 sprays every 4-12 hours.

Example 3

Intracellular cAMP Stimulation Assay

Human Y-79 retinoblastoma cells are grown in RPMI 1640 medium with 15% FBS. Measures of cAMP accumulation are performed by using NEN Adenylyl Cyclase FlashPlate kit (SMP004). The cells are separated from culture medium, washed twice with PBS (150×g, 8 min), resuspended (2E+6 cells/ml) in Stimulation Buffer (provided in the kit), and then added to 96-well FlashPlates, (50,000 cells per well). Various concentrations of test compounds are incubated with the cells for 20 min prior to the addition of hCRF (30 nM). The total assay volume is 100 µl. The assay is terminated after 20 min after addition of the hCRF by addition of Detection Buffer and [$^{125}$I]cAMP. After 2 hr at room temperature the mixtures are aspirated and the bound radioactivity is measured with a Packard TopCount. The potency ($IC_{50}$ values) of test compounds in inhibiting the hCRF-stimulated accumulation of cAMP is determined by nonlinear regression analyses with interactive curve-fitting procedures.

Example 4

CRF1 Receptor Binding Assay

Human IMR-32 neuroblastoma cells are grown to 80% confluence in MEM medium containing 10% heat-inactivated FBS, 1mM Sodium Pyruvate, and 0.1 mM nonessential amino acids. Cell membranes are prepared according to the method of Dieterich and DeSouza (1996). The cells (~5E+9) are resuspended in 10 volumes of wash buffer (5 mM Tris HCl, 10 mM $MgCl_2$, 2 mM EGTA, pH 7.4 at RT), homogenized with a Polytron, and then centrifuged at 45,000 G for 20 min at 4° C. The membrane pellets are washed twice with wash buffer (45,000 G for 20 min at 4° C.) and then resuspended (50 mM Tris HCl, 10 mM MgCl$_2$, 2 mM EGTA, pH 7.4 at RT). Protein concentration is determined using Pierce reagents and BSA as standard. Aliquots of 1-1.5 mL are stored at −80° C. until binding assay.

The competition binding assay is performed in a final volume of 250 μl, which contains assay buffer (50 mM Tris-HCl, 10 mM MgCl$_2$, 2 mM EGTA, 0.2% BSA, 0.1 mM bacitracin and 100 kIU/mL aprotinin pH 7.2 at R.T.), 0.05 nM [$^{125}$I] Tyr$^0$-ovine CRF (Du Pont New England Nuclear), 50 μg of membrane protein, and test compound at various concentrations. Non-specific binding is determined with 1 uM hCRF. Binding reactions are terminated after 2 hr incubation at 25° C. by filtering through 96-w GF/C filter plate using a Packard Harvester (Filtermate 196). The 96-w filter plate is pre-treated with 0.3% polyethyleneimine and pre-washed with washing buffer (50 mM Tris-HCl, 10 mM MgCl$_2$, 2 mM EGTA, 0.2% BSA, pH 7.2 at 4° C.). Unbound radioactivity is removed by four rapid washes (0.8 ml/well) with wash buffer. The radioactivity is quantified using a Packard TopCount. Data are analyzed using non-linear iterative curve fitting to obtain IC$_{50}$ and Hill slope values. PKi values are derived from pIC$_{50}$ values (−log of IC$_{50}$).

The compounds of the present invention were active in receptor binding and functional assays. Representative activities (pK$_i$) are shown in Table 2.

TABLE 2

| Compound | pK$_i$ |
| --- | --- |
| [2-Methyl-6-(3-methyl-pyrazol-1-yl)-pyrimidin-4-yl]-(2,4,6-trichloro-phenyl)-amine | 5.97 |
| [2,5-Dimethyl-6-(3-propyl-pyrazol-1-yl)-pyrimidin-4-yl]-(2,4,6-trichloro-phenyl)-amine | 5.79 |
| [5-Chloro-2-methyl-6-(4-methyl-imidazol-1-yl)-pyrimidin-4-yl]-(2,4,6-trichloro-phenyl)-amine | 5.72 |

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

What is claimed is:

1. A compound of the formula II:

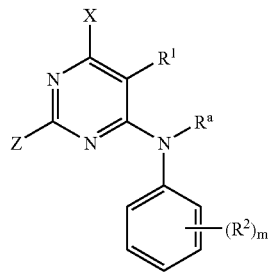

(II)

or a pharmaceutically acceptable salt thereof, wherein:

X is 3-methylpyrazol-1-yl, 3,5- dimethylpyrazol-1-yl, 4-chloro-3,5-dimethylpyrazol-1-yl, 3-propylpyrazol-1-yl, 3- butyl-4-propylpyrazol-1-yl, 2-methylimidazol-1-yl, 4-methylimidazol-1-yl or 4- phenylimidazol-1-yl;

R$^a$ is hydrogen or alkyl;

Z is alkyl;

R$^1$ is hydrogen, alkyl, alkoxy, haloalkyl, halo, hydroxy, cyano, nitro, —NR$^c$R$^d$, —C(O)NR$^c$R$^d$, alkylcarbonyl or alkylsulfonyl wherein R$^c$ and R$^d$ each independently is hydrogen or alkyl;

m is 3; and

R$^2$ is halo.

2. The compound of claim 1, wherein Z is methyl.

3. The compound of claim 1, wherein R$^a$ is hydrogen.

4. The compound of claim 1, wherein X is 3- methylpyrazol-1-yl, 3,5 -dimethylpyrazol-1-yl, 4-chloro-3,5-dimethylpyrazol-1-yl, 3- propylpyrazol-1-yl, or 3 -butyl-4-propylpyrazol-1-yl.

5. The compound of claim 1, wherein R$^1$ is hydrogen, alkyl or halo.

6. The compound of claim 5, wherein R$^1$ is hydrogen, methyl or chloro.

7. The compound of claim 1, wherein R$^a$ is hydrogen.

8. The compound of claim 1, wherein X is 2- methylimidazol-1-yl, 4-methylimidazol-1-yl or 4-phenylimidazol-1-yl.

9. A compound of formula (III):

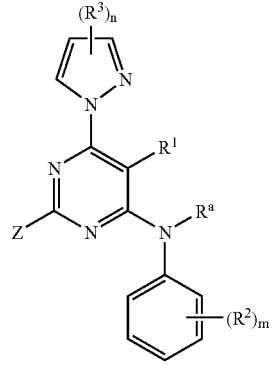

(III)

wherein:

m is 3;

n is from 0 to 3;

R is $^2$ halo;

Z is alkyl;

R$^1$ is hydrogen, alkyl, alkoxy, haloalkyl, halo, hydroxy, cyano, nitro, —NR$^c$R$^d$, —C(O)NR$^c$R$^d$, alkylcarbonyl or alkylsulfonyl wherein R$^c$ and R$^d$ each independently is hydrogen or alkyl; and each R$^3$ independently is alkyl, optionally substituted phenyl or halo.

10. The compound of claim 9, wherein n is 1 or 2.

11. The compound of claim 9 wherein R$^1$ is hydrogen, alkyl or halo.

12. The compound of claim 9, wherein n is 1 and R$^3$ is methyl or propyl.

13. The compound of claim 9, wherein n is 2, one of R$^3$ is propyl and the other is butyl.

14. A compound of formula (IV):

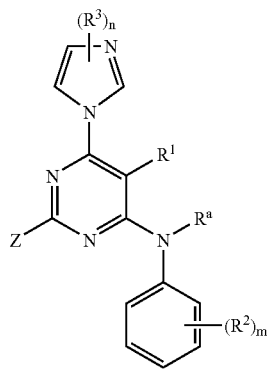

(IV)

wherein:
m is 3;
n is from 0 to 3;
R is ² halo;
Z is alkyl;

R¹ is hydrogen, alkyl, alkoxy, haloalkyl, halo, hydroxy, cyano, nitro, —NR$^c$R$^d$, —C(O)NR$^c$R$^d$, alkylcarbonyl or alkylsulfonyl wherein R$^c$ and R$^d$ each independently is hydrogen or alkyl; and each R³ independently is alkyl, optionally substituted phenyl or halo.

15. The compound of claim 14, wherein n is 1 and R³ is methyl.

16. The compound of claim 14, wherein n is 1 and R³ is phenyl.

17. The compound of claim 14 wherein R¹ is hydrogen, alkyl or halo.

18. A pharmaceutical composition, comprising a compound of claim 1 together with a pharmaceutically acceptable carrier.

19. A method for treating depression, said method comprising administering to a subject in need thereof a therapeutically effective amount of a compound of claim 1.

* * * * *